Figure 1:
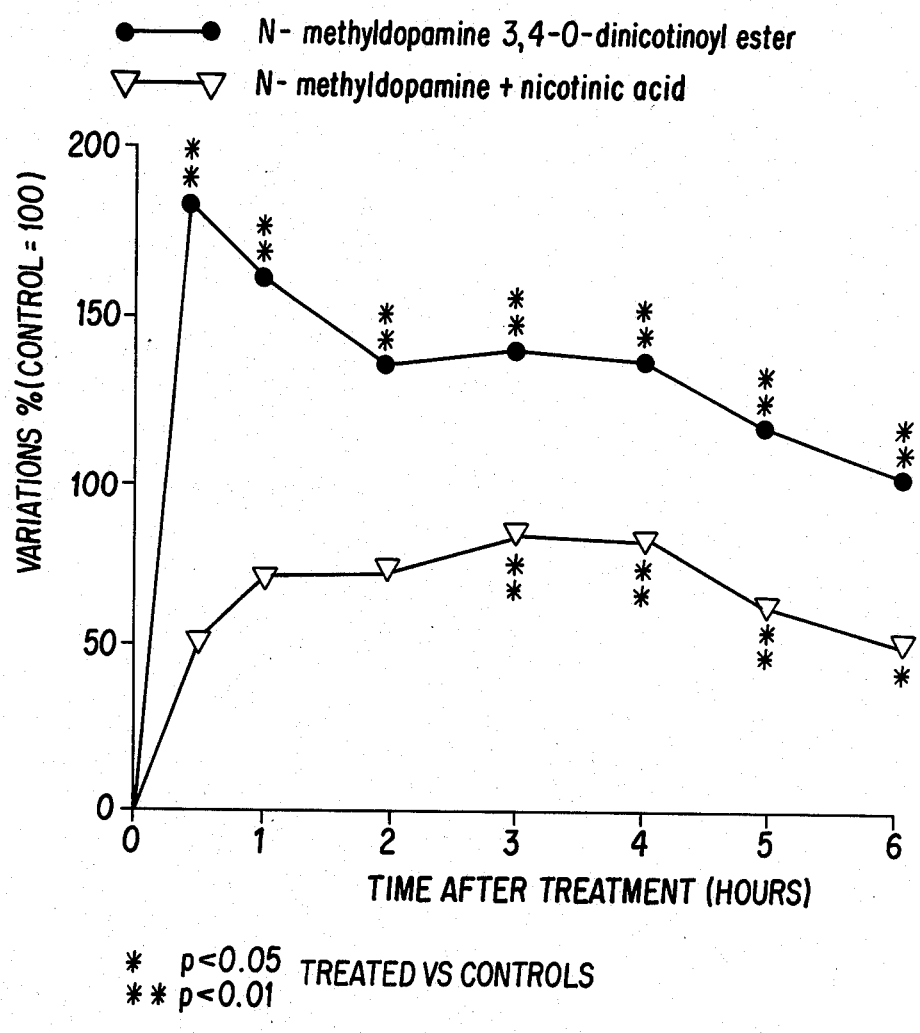

United States Patent [19]

Casagrande et al.

[11] Patent Number: 4,644,004

[45] Date of Patent: Feb. 17, 1987

[54] PYRIDYNECARBOXYLIC ESTERS OF DOPAMINE AND OF ITS N-ALKYL DERIVATIVES

[75] Inventors: Cesare Casagrande, Arese; Emilio Mussini; Vittorio Vecchietti, both of Milan, all of Italy

[73] Assignee: Simes S.p.A., Milan, Italy

[21] Appl. No.: 699,598

[22] Filed: Feb. 8, 1985

Related U.S. Application Data

[63] Continuation-in-part of Ser. No. 520,596, Aug. 5, 1983, abandoned.

[30] Foreign Application Priority Data

Aug. 6, 1982 [IT] Italy .............................. 22761 A/82

[51] Int. Cl.⁴ ................. C07D 401/02; A61K 31/455; A61K 31/44
[52] U.S. Cl. .................................... 514/332; 514/335; 546/261; 546/263
[58] Field of Search ................ 546/263, 261; 514/332, 514/335

[56] References Cited

U.S. PATENT DOCUMENTS 2,428,253 9/1947 Werder et al. ...................... 546/263

FOREIGN PATENT DOCUMENTS 4017022 of 1965 Japan .................................. 546/263

OTHER PUBLICATIONS

Farmasimes Chem. Abst. 88:22405e.

Primary Examiner—Jane T. Fan
Attorney, Agent, or Firm—Stevens, Davis, Miller & Mosher

[57] ABSTRACT

Pyridinecarboxylic esters of dopamine and of its N-alkyl derivatives, salts thereof with pharmaceutically acceptable organic or inorganic acids, process for preparing them and pharmaceutical compositions containing them which are particularly useful in the treatment of cardiovascular and renal disorders.

3 Claims, 2 Drawing Figures

PYRIDYNECARBOXYLIC ESTERS OF DOPAMINE AND OF ITS N-ALKYL DERIVATIVES

This application is a continuation-in-part of application Ser. No. 520,596 filed on Aug. 5, 1983 now abandoned.

This invention relates to new pyridinecarboxylic esters of dopamine and of its N-alkyl derivatives as well as to their pharmaceutically acceptable salts. The products according to this invention are active in the treatment of cardiovascular and renal disorders also when orally administered. Furthermore this invention relates to the process for preparing the new products and the pharmaceutical compositions containing them.

More particularly the new products according to this invention have general formula

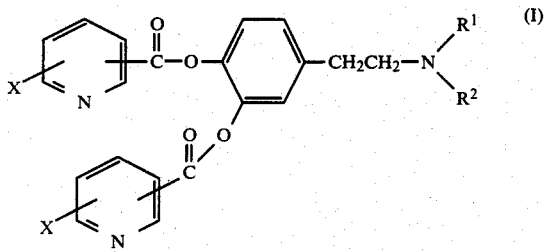

wherein

X is H, halogen, straight or branched alkyl having from 1 to 4 C atoms or alkoxy having from 1 to 4 C atoms, R1 and R2 are the same or different H or straight or branched alkyl having from 1 to 4 C atoms.

The products according to this invention may be prepared by reacting a product of formula

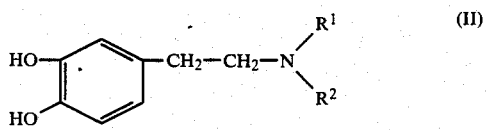

wherein R1 and R2 have the above mentioned meaning, with a pyridinecarboxylic acid of formula

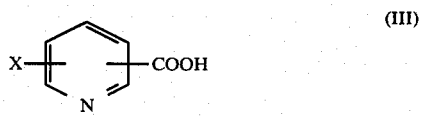

wherein X has the above mentioned meaning in the presence of condensation agents, or with a reactive derivative of the acid (III) such as, for example, a halide, an anhydride or an activated ester.

When R1 and/or R2 are hydrogen the acylation of the product (II) is carried out in such a way to avoid the simultaneous acylation of the amino group of the product (II).

To this end the reaction may be carried out in a strongly acid medium so that the amino group is completely protonated.

Suitable acids are either the inorganic acids such as a hydrogen halide or the organic acids such as trifluoroacetic and methanesulfonic acid.

Alternatively, the undesired acylation of the amino group may be avoided by means of a suitable protective group such as the carbobenzyloxy group which can be easily removed after completion of the esterification of the phenolic hydroxy groups.

When the esterification of the product (II) is carried out with an acid (III) in the presence of a condensation agent such as dicyclohexylcarbodiimide, the reaction is carried out at a temperature comprised between 0° C. and the reflux temperature of the reaction mixture.

As esterification agent it can be used also a halide of the acid (III), preferably a chloride or a bromide, by working at a temperature between −15° C. and the boiling temperature of the reaction mixture. The reaction can be promoted by adding suitable basic compounds which bind the hydrogen halide which is formed, such as, for example, alkaline and alkaline earth carbonates and bicarbonates or organic bases, like pyridine, trimethylamine triethylamine and dimethylaminopyridine; obviously the base is not added when the protection of the amino group of the product (II) is made by protonation but only when the amino group of the product (II) is dialkylated or protected by means of a suitable protective group; the volatile organic bases such as pyridine may be used in excess, then they act also as solvents.

Other esterification agents which may be used according to this invention are the simple and the mixed anhydrides or the activated esters of the acid (III).

In this case the esterification is preferably carried out at a temperature comprised between −15° C. and the reflux temperature of the reaction mixture. The esterification with anyone of the above mentioned agents (acid halides, anhydrides and esters) may be carried out in an inert organic solvent, such as a hydrocarbon, more particularly a halogenated hydrocarbon such as methylene chloride, an acylic or cyclic ether such as ethyl acetate or an amide such as dimethylformamide.

A further object of this invention are the salts of the compounds of formula I with organic or inorganic pharmaceutically acceptable acids such as methansulfonic, citric and tartaric acid.

In vivo and in vitro tests in the animals have shown that new compounds of formula I and their salts are endowed with diuretic activity, with direct vasodilating activity particularly on the renal artery, with indirect vasodilating activity mediated by the vascular sympathetic terminations and consequent hypotensive activity as well as with positive inotropic activity. Therefore they are useful in the therapy of cardiac decompensation, renal insufficiency, hypertension, pathologic syndromes characterized by insufficient perfusion of vital organs.

Contrary to the compounds whose catecholamine system is not esterified, these compounds are well adsorbed by the gastroenteric tract and are active also by oral route.

It is well known that dopamine and its N-alkyl derivatives exhibit diuretic activity, direct vasodilating activity particularly on the renal artery, indirect vasodilating activity mediated by the vascular sympathetic terminations and consequent hypotensive activity as well as positive inotropic activity. The prevailing activity changes in accordance with the nature of the substituent; in dopamine prevail the inotropic activity as well as the diuretic and renal vasodilating activity. In the N,N-dialkyl-dopamines wherein at least one alkyl group is n-propyl, prevail the indirect vasodilating activity and the renal vasodilating activity but the last is lower than that of dopamine.

The pharmacological activity of the compounds (I) is clearly higher than that of the mixtures of the compounds (II) and (III).

DIURETIC EFFECT IN RATS

The compounds under investigation has been dissolved in water and orally administered to three groups of 10 animals each.

- 1st group: control (water, 2 ml/kg)
- 2nd group: N-methyl-dopamine 3,4-0-dinicotinoyl ester; 0,29 mmol/Kg = 141 mg/kg
- 3rd group: N-methyl-dopamine 0,29 mmol/kg + nicotinic acid 0,58 mmol/kg (60 + 71 mg/kg).

for each group 5 couples of rats have been used.

The volume of the excreted urine has been measured after 30 minutes, 1 hour and each subsequent hour till six hours after the treatment. The mean value and the standard error have been computed for each group. The significance of the differences between the mean values in the treated animal against the controls has been tested by Dunnett's test.

The results are shown by FIG. 1: N-methyldopamine, 3,4-0-dicotinoyl ester has an increase in diuresis higher than that observed after administration of a mixture of N-methyldopamine and of nicotinic acid. Hypotensive effect in spontaneously hypertensive rats (SHR)

The compound under investigation has been dissolved in water and orally administered daily for three days to 5 groups of 4 animals each.

- 1st group: control (water, 1 ml/kg)
- 2nd group: N,N-di-n-propyldopamine 3,4-0-dinicotinoyl ester; 0,29 mmol/kg = 162 mg/kg
- 3rd group: N,N-di-n-propyopamine 0,29 mmol/kg + nicotinic acid 0,50 mmol/kg (92 + 71.4 mg/kg)
- 4th group: nicotinic acid 0,58 mmol/kg
- 5th group: N,N-di-n-propyldopamine 0,29 mmol/kg.

The arterial systolic pressure has been measured 1,2,3,5 and 8 hours after the 1st and the 3rd administration. The differences between the basal and the measured values have been computed. The mean value and the standard error have been computed for each group. The significance and the differences between the mean pressure variation (mm Hg) observed in treated animals against that observed in controls has been tested by Dunnett's test.

Figure 2:
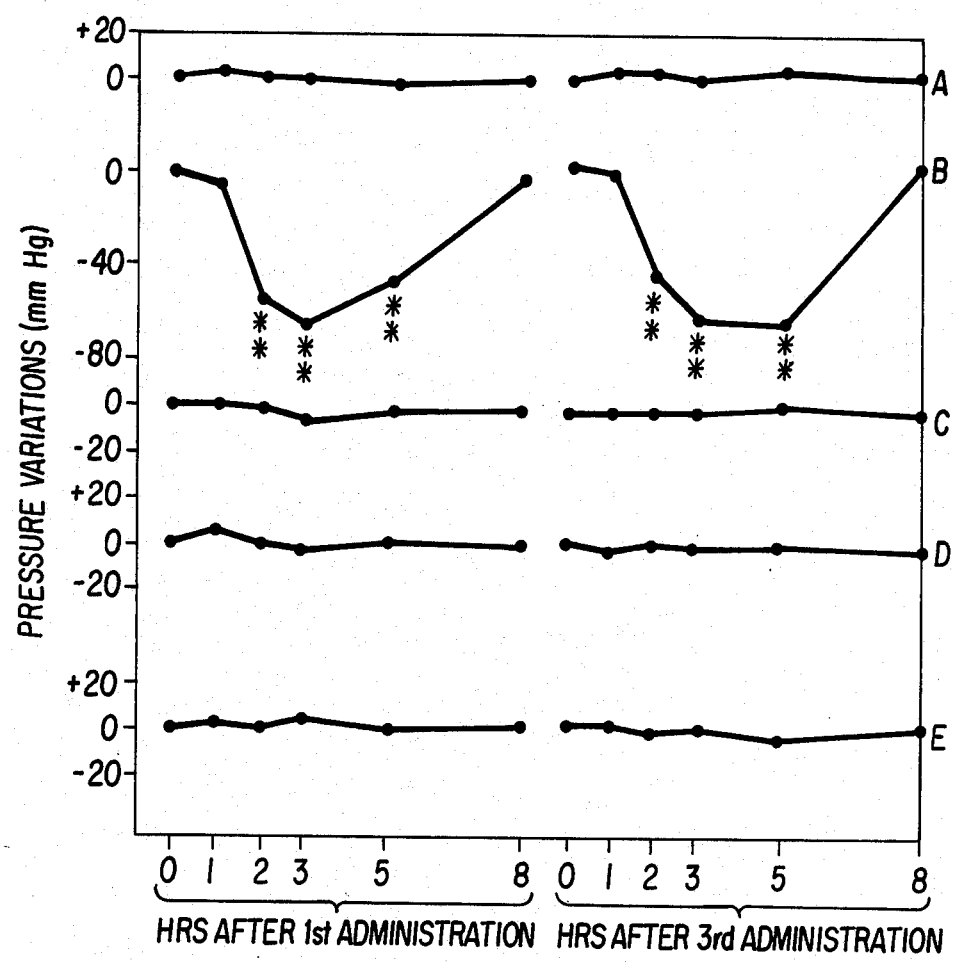

The results are shown by FIG. 2.

N,N-di-n-propyldopamine-3,4-dinicotinoyl ester exhibits a clear hypotensive effect either after the first or the third administration.

On the contrary N,N-di-n-dipropyldopamine alone, nicotinic acid alone as well as their mixture have shown no effect.

Preliminary tests have confirmed these activity in the man. Finally, it is an object of this invention to provide pharmaceutical compositions containing, as active ingredients, the compounds of the formula I or their pharmaceutically acceptable salts together with pharmaceutically acceptable organic or inorganica, solid or liquid carriers.

The pharmaceutical compositions may be in solid form such as tablets, dragees, capsules, powders, granular, or in liquid form as solution, suspensions, emulsions.

They may be also prepared in such a way that the release of the drug is prolonged after the administration.

In addition to the usual carriers they may include preserving, stabilizing, wetting or emulsifying agents, salts for regulating the osmotic pressure, buffers, dye-stuffs or flavouring agents.

They are prepared according to known methods and may further contain other therapeutic agents.

The precise dose of the compound of the invention administered depends inter alia on the age and weight of the patient and the severity of the condition. This can be determined by routine experimentation.

Preferably, the compositions will contain the compound of formula (I) in an amount sufficient to produce the desired pharmacodynamic activity. Preferably, the compositions will contain the compound of formula (I) (or the salt calculated as the free base) in an amount selected from 20 mg to 400 mg and will be administered to an adult from 1 to 4 times per day.

The following examples are given to illustrate the present invention without limiting it in any way.

EXAMPLE 1

A solution of 10 g (33 mmols) of N-methyl-N-carbobenzoxy-dopamine and of 24 g (134 mmols) of nicotinoyl chloride hydrochloride in 150 ml of pyridine is maintained under stitting at 80° C. for 4 hours.

The reaction mixture is then poured into water, made alkaline with sodium bicarbonate, extracted with methylene chloride, dried over sodium sulfate, filtered, evaporated.

The residue is purified via chromatography on silica gel column (eluent, methylene chloride/ethanol = 98/2) to afford 3,4-0-di-nicotinoyl-N-methyl-N-carbobenzoxy dopamine (yield, 38,2%) as an oil chromatographically pure (T.L.C. on silica gel, solvent: acetone/toluene/water/butanol/acetic acid = 1/1/1/1/1, $I_2$ detection, mass spectrum: M+ at 511 m/e).

EXAMPLE 2

By working as described in the Example 1, but replacing the nicotinoyl chloride hydrochloride with an equivalent amount of isonicotinoyl chloride hydrochloride and using as eluent for the column chromatography a mixture of methylene chloride = 99/1, 3,4-0-isonicotinoyl-N-methyl-N-carbobenzoxy-dopamine is obtained as an oil chromatographically pure (T.L.C. on silica gel, solvent: methylene chloride/ethyl acetate = 45/5, $I_2$ detection, mass spectrum: M+ at 511 m/e).

EXAMPLE 3

By working as described in Example 1, but replacing the nicotinoyl chloride hydrochloride with an equivalent amount of 5-bromo-nicotinoyl chloride hydrochloride and using as eluent for the column chromatography a mixture of methylene chloride/ethanol = 99/1, 3,4-0-di-(5-bromo-nicotinoyl)-N-methyl-N-carbobenzoxy-dopamine is obtained as an oil chromatographically pure (T.L.C. on silica gel, solvent: methylene chloride/ethyl acetate + 40/5, $I_2$ detection, mass spectrum: M+ at 669 m/e).

EXAMPLE 4

By working as described in Example 1, but replacing the N-methyl-N-carbobenzoxy-dopamine with an equivalent amount of N-carbobenzoxy-dopamine, 3,4-dinicotinoyl-N-carbobenzoxy-dopamine is obtained (m.p. 86°-90° C., from benzene).

EXAMPLE 5

5 g (0.7 mmols) of 3,4-0-dinicotinoyl-N-methyl-N-carbobnzoxy-dopamine prepared as described in Example 1, and 750 mg of 10% Pd/C in 50 ml of trifluoroacetic acid are hydrogenated in a Parr apparatus at room pressure and room temperature, for 1 hour. After filtration and evaporation, the residue is dissolved in methylene chloride and washed with 10% sodium bicarbonate, dried over sodium sulfate and evaporated.

The thus obtained product is dissolved in ethyl acetate and treated with an excess of a solution of hydrochloric acid in ethyl ether. The solvent is removed by evaporation and the residue is crystallized from methanol/ethyl acetate to afford 3,4-0-di-nicotinoyl-N-methyl-dopamine trihydrochloride (yield, 80%, m.p. 202°-203° C., from methanol/ethyl acetate).

This product may be also obtained by refluxing a solution of 3,4-di-0-dinicotinoyl-N-methyl-N-carbobenzoxy-dopamine in trifluoroacetic acid.

EXAMPLE 6

By working as described in example 5, but replacing 3,4-0-di-nicotinoyl-N-methyl-N-carbobenzoxy-dopamine with an equivalent amount of 3,4-0-di-isonicotinoyl-N-methyl-N-carbobenzoxy-dopamine obtained as described in Example 2, 3,4-0-di-isonicotinoyl-N-methyl-dopamine trihydrochloride is obtained (m.p. 132°-134° C., from methanol/ethyl acetate).

EXAMPLE 7

By working as described in example 5, but replacing 3,4-0-di-nicotinoyl-N-methyl-N-carbobenzoxy-dopamine with an equivalent amount of 3,4-0-di-(5-bromonicotinoyl)-N-methyl-N-carbobenzoxy-dopamine obtained as described in example 3, 3,4-0-di-(5-bromonicotinoyl)-N-methyl-dopamine trihydrochloride (m.p. 165°-167° C., from methanol/ethyl acetate) is obtained.

EXAMPLE 8

By working as described in example 5, but replacing 3,4-0-di-nicotinoyl-N-methyl-N-carbobenzoxy-dopamine with an equivalent amount of 3,4-0-dinicotinoyl-N-carbobenzoxy-dopamine obtained as described in Example 4, 3,4-0-dinicotinoyl-dopamine trihydrochloride (m.p. 172°-174°, from methanol/ethyl acetate) is obtained.

EXAMPLE 9

A solution of 3 g (9.4 mmols) of N-di-n-propyl-dopamine hydrobromide, 5,3 g (29,7 mmols) of nicotinoyl chloride hydrochloride, 50 mg (0.4 mmol) of dimethylamino-pyridine and 45 ml of pyridine are maintained under stirring at 80° C. for 12 hours.

The solvent is removed under vacuum, the residue is treated with methylene chloride, washed with sodium bicarbonate 1N, dried over sodium sulfate, filtered and evaporated.

The residue is dissolved in methanol and treated with a solution of hydrochloric acid in methanol; the solution is diluted with ethyl acetate to afford 3,4-0-dinicotinoyl-N-di-n-propyl-dopamine trihydrochloride (yield, 65%, m.p. 145°-148° C., from ethanol/ethyl acetate; the corresponding picrolonate melts at 136°-138° C., from 95% ethanol).

EXAMPLE 10

By working as disclosed in Example 9, but replacing N-di-n-propyl-dopamine hydrobromide with an equivalent amount of N-n-propyl-N-n-butyl dopamine hydrobromide, 3,4-0-dinicotinoyl-N-n-propyl-N-n-butyl-dopamine trihydrochloride is obtained. (m.p. 154°-156° C. from ethyl acetate; the corresponding picrolonate melts at 131°-133° C.; from 95% ethanol).

EXAMPLE 11

Each coated tablet contains: mg
3,4-0-dinicotinoyl-N,N-di-n-propyldopamine hydrochloride: 50
microgranulated cellulose: 23.5
polyvinylpyrrolidone: 1.5
cross-linked polyvinylpyrrolidone: 3
hydrogenated castor oil: 1
hydroxypropylmethylcellulose: 3.57
polyethylene glycol 6,000: 0.68

The active ingredient and microgranulated cellulose are mixed and granulated with an aqueous solution of polyvinylpyrrolidone. The mixture is partially dried and then granulated and dried until the redisual humidity is lower than 1%. Cross-linked polyvinylpyrrolidone and hydrogenated castor oil are added and mixed. The mixture is then tabletted.

The tablets are loaded into a rotating bassin machine together with a solution of hydroxypropylmethylcellulose and polyethylene glycol 6,000 and treated until their weight has been increased of about 3%;

EXAMPLE 12

Each coated tablet contains: mg
3,4-0-dinicotinoyl-N-methyldopamine hydrochloride: 100
microgranulated cellulose: 47
polyvinylpyrrolidone: 3
cross-linked polyvinylpyrrolidone: 6
hydrogenated castor oil: 1
hydroxypropylmethylcellulose: 7.14
polyethylene glycol 6,000: 1.34

These coated tablets are prepared using the same procedure as described in Example 11 above.

EXAMPLE 13

Each slow-release tablet contains: mg
3,4-0-dinicotinoyl-N,N-di-n-propyldopamine hydrochloride: 250
hydrogenated castor oil: 40
polyvinylpyrrolidone: 10
carnauba wax: 40
ethylcellulose: 4
hydroxypropylmethylcellulose: 3
silica gel: 3

The active ingredient, hydrogenated castor oil and polyvinylpyrrolidone are mixed together and then with methylene chloride. The mixture is granulated and dried in a cabinet under forced air.

The carnauba wax is added and mixed; the mixture is tabletted.

The tablets are loaded into a rotating bassin together with a solution of ethylcellulose and hydropropyl methyl cellulose in methylene chloride and isopropanol in which is suspended the silica gel.

We claim:
1. A product of formula (I)

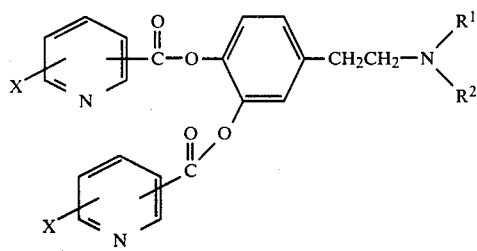

wherein X is hydrogen, halogen, straight or branched alkyl having from 1 to 4 C atoms or alkoxy having from 1 to 4 C atoms;

R1 and R2 are the same or different hydrogen, or straight or branched alkyl having from 1 to 4 C atoms, or a salt thereof with an organic or inorganic pharmaceutically acceptable acid, and being useful in the treatment of cardiovascular and renal disorders.

2. A pharmaceutical composition useful in the treatment of cardiovascular and renal disorders comprising a product of formula (I):

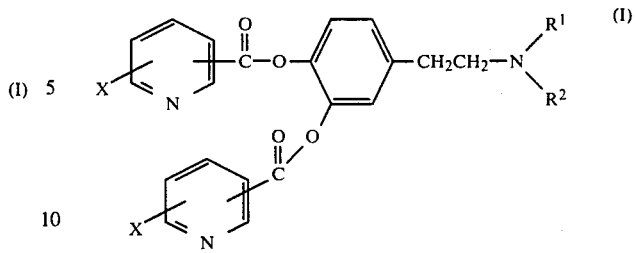

wherein X is hydrogen, halogen, straight or branched alkyl having from 1 to 4 C atoms or alkoxy having from 1 to 4 C atoms, R1 and R2 are the same or different hydrogen, or straight or branched alkyl having from 1 to 4 C atoms, or a pharmaceutically acceptable salt thereof, together with at least one pharmaceutically acceptable carrier.

3. A pharmaceutical composition useful in the treatment of cardiovacular and renal disorders comprising from 20 to 400 mg of a product of formula (I)

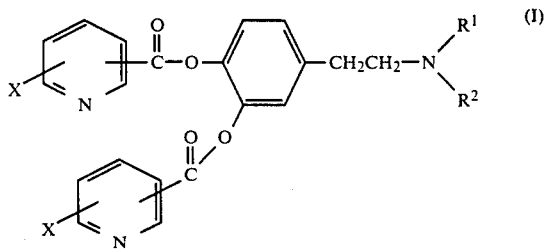

wherein X is hydrogen, halogen, straight or branched alkyl having from 1 to 4 C atoms or alkoxy having from 1 to 4 C atoms, R1 and R2 are the same or different hydrogen, or straight or branched alkyl having from 1 to 4 C atoms, or the corresponding amount of a pharmaceutically acceptable salt thereof, together with at least one pharmaceutically acceptable carrier.

* * * * *